United States Patent
Hirose et al.

(10) Patent No.: US 8,940,525 B2
(45) Date of Patent: Jan. 27, 2015

(54) DEVICE FOR A MEMBRANE ASSAY

(75) Inventors: Takanori Hirose, Gosen (JP); Koichi Inano, Gosen (JP); Hideharu Simizu, Gosen (JP)

(73) Assignee: Denko Seiken Co., Ltd., Tokyo (JP)

( * ) Notice: Subject to any disclaimer, the term of this patent is extended or adjusted under 35 U.S.C. 154(b) by 0 days.

(21) Appl. No.: 13/283,047

(22) Filed: Oct. 27, 2011

(65) Prior Publication Data

US 2012/0077261 A1    Mar. 29, 2012

Related U.S. Application Data

(63) Continuation of application No. PCT/JP2010/057389, filed on Apr. 26, 2010.

(30) Foreign Application Priority Data

Apr. 28, 2009 (JP) ................................. 2009-109724

(51) Int. Cl.
| | |
|---|---|
| C12M 1/34 | (2006.01) |
| C12M 3/00 | (2006.01) |
| G01N 33/53 | (2006.01) |
| G01N 33/546 | (2006.01) |
| G01N 33/558 | (2006.01) |

(Continued)

(52) U.S. Cl.
CPC ........ G01N 33/558 (2013.01); G01N 33/54386 (2013.01); G01N 33/561 (2013.01)
USPC ..... 435/287.2; 436/510; 436/533; 435/287.1; 435/287.7; 435/287.8

(58) Field of Classification Search
USPC .......... 435/287.2, 283.1–309.4; 436/510, 533
See application file for complete search history.

(56) References Cited

U.S. PATENT DOCUMENTS

| | | | |
|---|---|---|---|
| 2004/0092036 A1* | 5/2004 | Chen et al. ..................... | 436/514 |
| 2005/0147657 A1* | 7/2005 | Canada et al. ................ | 424/445 |
| 2006/0160064 A1* | 7/2006 | Carbonell ......................... | 435/4 |

FOREIGN PATENT DOCUMENTS

| | | |
|---|---|---|
| JP | 10-90267 A | 4/1998 |
| JP | 3134231 B2 | 2/2001 |

(Continued)

OTHER PUBLICATIONS

International Search Report (PCT/ISA/210, PCT/ISA/220) issued in PCT/JP2010/057389 dated Jun. 1, 2010.

(Continued)

*Primary Examiner* — Nathan Bowers
*Assistant Examiner* — Lydia Edwards
(74) *Attorney, Agent, or Firm* — Lowe Hauptman & Ham, LLP

(57) ABSTRACT

Disclosed is a simple device for a membrane assay using the lateral flow immunoassay method, whereby a subject to be detected can be detected at a high sensitivity, provided with, as a label drying pad, a substrate which has a higher tensile strength than glass fiber and can well release a label. The present invention provides a simple membrane assay device, comprising: a supporting board, a sample supply part, a label containing a labeling component which labels a subject to be detected, a development part formed with a detection part which includes a trapping reagent for detecting or quantifying the subject to be detected, and an absorption part, wherein a non-woven fabric which includes fibers having a fiber diameter of 0.05 to 10 μm is used in the labeling component part.

10 Claims, 4 Drawing Sheets

(51) Int. Cl.
*G01N 33/543* (2006.01)
*G01N 33/561* (2006.01)

(56) References Cited

FOREIGN PATENT DOCUMENTS

| | | |
|---|---|---|
| JP | 2005-9888 A | 1/2005 |
| JP | 2005-509852 A | 4/2005 |
| JP | 2007-255944 A | 10/2007 |
| JP | 2008-203135 A | 9/2008 |
| WO | 90/09592 A1 | 8/1990 |
| WO | 03/042659 A2 | 5/2003 |
| WO | 2006/080438 A1 | 8/2006 |
| WO | 2011/063395 A2 | 5/2011 |

OTHER PUBLICATIONS

Written Opinion of the International Searching Authority issued in PCT/JP2010/057389 dated Jun. 1, 2010.
Notification of Transmittal of the International Search Report and the Written Opinion of the International Searching Authority, or the Declaration issued in PCT/JP2010/057389 dated Jun. 1, 2010.
"Rapid Lateral Flow Test Stripes", Millipore, 2008, XP002884173, URL:http://www.millipore.com/publications.nsf/a73664f9f981af8c852569b9005b4eee/348ee7096d93729b85256bf40066a40d/$FILE/tb500en00.pdf, [retrived on Sep. 25, 2012], p. 20, col. 1, para 2; fig 1.
The Extended European Search Report issued Oct. 15, 2012 in corresponding European Patent Application.

* cited by examiner

DEVICE FOR A MEMBRANE ASSAY

CROSS REFERENCE TO RELATED APPLICATIONS

This application is based upon and claims the benefit of priority from the prior Japanese Patent Application No. 2009-109724, filed on Apr. 28, 2009, and PCT Application No. PCT/JP2010/057389, filed on Apr. 26, 2010, the entire contents of which are incorporated herein by reference.

FIELD

The present invention is related to a simple test kit used in a clinical assay. In particular, the present invention is related to a simple device for a membrane assay which uses a lateral flow immunoassay method.

BACKGROUND

In recent years, simple test reagents or kits for performing a variety of tests such as for the presence of pathogen infection such as a virus or bacteria, or pregnancy are being developed. Detection or quantification of a pathogen component or hormone is the subject of these tests. Many of these simple test reagents are cheap, simple to operate and do not require specific equipment or devices.

For example, pregnancy test reagents are sold at general chemists and pathogen test reagents are widely used in hospitals and surgeries. The importance of simple assay reagents at medical facilities is increasing since medical measures can be taken at an early stage if the presence of an infection is confirmed in a pathogen test.

Presently, an immunoassay method which uses an antigen-antibody reaction is commonly known as a simple test method and a lateral flow test reagent is sold widely. The principle of this test reagent is a method in which a detection sample including a subject to be detected is developed on a nitrocellulose membrane in a horizontal direction, and a composite of a label which binds specifically with the subject to be detected is formed on the membrane. It is possible to detect or quantify the subject to be detected by detecting or quantifying this label.

One form of the lateral flow immunoassay method includes supplying a certain amount of a specimen sample which includes the subject to be detected to a test device arranged with a detection part in which an antibody which specifically binds to a subject to be detected is solid phased as a trapping agent on a membrane strip of nitrocellulose etc, and a labeling component part which includes a label for specifically binding to a subject to be detected, the specimen sample is developed while forming a composite of the subject to be detected and the label, and the label is detected or quantified by trapping the composite with the detection part.

In an assay system which uses the above described membrane, a method in which a gold particle is labeled on an antibody which specifically binds with a subject to be detected as a label is conventionally used. However, recently, an assay system has been established which uses a colored latex particle, a phosphor latex particle and a magnetic latex particle instead of a gold particle and the assay subject continues to expand. In particular, an effective and simple test reagent is greatly expected in the lateral flow immunoassay method, because a wide ranging subject pathogen microbial antigen can be assayed if an antibody can be prepared.

Generally, the time required for an assay (reaction) in the lateral flow immunoassay method is 5 to 15 minutes. A quicker and more sensitive assay method is being demanded as a simple test which requires speed in the detection and treatment of viruses such as the influenza virus, adenovirus and norovirus and thus many improvements are being researched.

The label is used in labeling a latex particle on an antibody which specifically binds to a subject to be detected as a marker and in a state in which the later particle is freeze dried or warm air dried (including natural drying). However, time is required to release and reconstruct the label when detection testing and because the label is sometimes left without being developed, there is a problem in rapid, highly sensitive detection.

As a means for solving this problem, Japanese Laid Open Patent 2008-203135 for example discloses rapidly reconstructing and developing a label within a specimen sample using a surface activating agent and suppressing autoagglutination of a latex particle during a drying process by including a sugar chain.

However, when focusing on a substrate which is included with a label, a material in which glass fiber which is often used as a substrate included with a label such as a latex particle is processed into a sheet has good label release yet tension strength is weak and manufacturing process restrictions are received. In addition, while there are materials such as synthetic fibers which have strong tension strength, release of a label from a label drying pad on which the label is dried on the substrate is poor and are not suited to quick, highly sensitive and simple detection reagents. As a result, until recently, a substrate with good label release and strong tension strength was not used as a label drying pad.

SUMMARY

To provide a simple device for a membrane assay using the lateral flow immunoassay method, whereby a subject to be detected can be detected at a high sensitivity, provided with, as a label drying pad, a substrate which has a higher tensile strength than glass fiber and can well release a label.

According to one embodiment, a simple device for a membrane assay including a supporting board, a sample supply part, a labeling component part containing a labeling component which labels a subject to be detected, a development part formed with a detection part which includes a trapping reagent for detecting or quantifying the subject to be detected, and an absorption part, wherein a non-woven fabric which includes fibers having a fiber diameter of 0.05 to 10 μm is used in the labeling component part.

The simple device for a membrane assay wherein the fibers may be synthetic fibers.

The simple device for a membrane assay wherein the non-woven fabric may have a plurality of fibers adhered to one another.

The simple device for a membrane assay wherein the non-woven fabric may be formed by split fibers in which a split fiber type composite fiber comprised of a plurality of fiber components adhered to each other are split fiber processed.

The simple device for a membrane assay wherein the split fiber type composite fiber may have a structure arranged with a plurality of second fiber components with a fiber diameter from 1 μm to 10 μm on a cross sectional exterior periphery of a first fiber component with a fiber diameter from 6 μm to 20 μm.

The simple device for a membrane assay wherein the labeling component may be labeled by any one of a gold colloid particle, a platinum colloid particle, a latex particle, a magnetic particle or an enzyme.

The simple device for a membrane assay wherein the labeling component and the trapping reagent may be antibody or antigen binding fragments which bind with the subject to be detected.

The simple device for a membrane assay wherein the subject to be detected may be a microbe, a biological derived material which is a clinical marker, a pesticide, an environmental hormone or a decomposed matter of these.

The simple device for a membrane assay wherein the subject to be detected may be detected or quantified using a lateral flow membrane assay method.

The simple device for a membrane assay may further comprise a verification part for verifying that the labeling component is released to the development part.

The simple device for a membrane assay wherein a plurality of types of labeling component and trapping reagent may be used respectively for detecting a plurality of types of the subject to be detected.

Here a composite fiber refers to a plurality of fiber components each linked in the length direction of the fibers wherein side surfaces of fibers are mutually attached, and may also include two or more materials with different fiber components.

Furthermore, a split fiber type composite fiber refers to a composite fiber which includes a structure in which each fiber component which forms the composite fiber can be split.

In addition, split fiber processing refers to splitting split fiber type composite fiber into each fiber component by, for example, a method of hitting high pressure water or heating the split fiber type composite fibers, or a method which matches an adhesion method between the fiber components such as a method for immersing in a solvent, and each split fiber component is called a split fiber.

Furthermore, it is preferred that the non-woven fabric is manufactured by spunbonding.

EXPLANATION OF THE REFERENCE SYMBOLS

Figure 1:
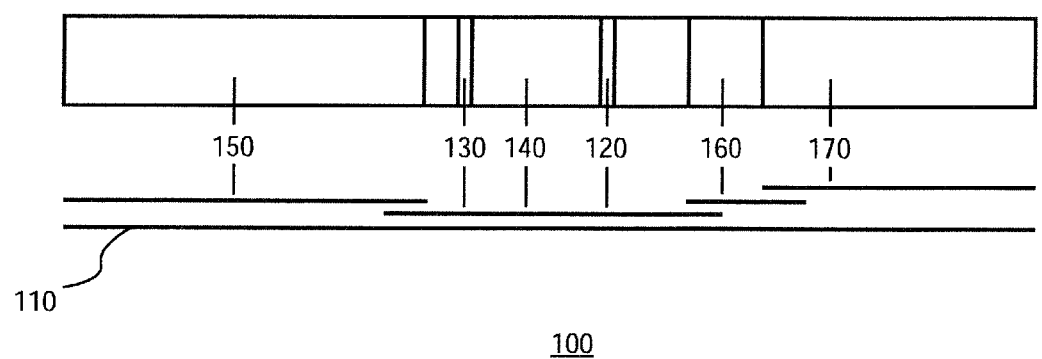
FIG. 1 is an exemplary diagram of a simple device for a membrane assay 100 related to one embodiment of the present invention.

100 simple membrane assay device related to the first embodiment
110 plastic plate
120 detection part
130 control line
140 nitrocellulose membrane
150 absorption pad
160 label drying pad
170 sample supply pad
200 split fiber type composite fiber
201 core fiber component
202 fiber component of ultrafine split fiber
250 split fiber processed split fiber type composite fiber
300 simple membrane assay device related to the second embodiment
321 detection part A
323 detection part B
330 control line
360 label drying pad

DESCRIPTION OF EMBODIMENTS

As described above, glass fiber or non-woven fabric is generally used in a label drying pad. However, while release of a label is good in the case if processing the glass fiber into a sheet, tensile strength is weak and manufacturing restrictions are received. In addition, in the case where a synthetic fiber is used, tensile strength is good but release of the label is poor. A method for overcoming these defects was keenly examined.

For example, a non-woven fabric comprised of a composite material of glass fiber and another material may be possible in order to provide the tensile strength required for glass fiber. However, improvements in the release efficiency of a label using a merely a combination with a synthetic fiber non-woven fabric cannot be expected.

Thus, improving the release efficiency of a label using a synthetic fiber non-woven fabric was examined. Comparing the characteristics of a synthetic fiber and a glass fiber, a method of forming a label drying pad using an ultrafine synthetic fiber non-woven fabric was found because glass fiber has a small fiber diameter.

The label drying pad of a labeling component part related to the present invention is formed by a non-woven fabric in which a plurality of ultrafine fiber components are adhered to each other, which has strong tensile strength. A method of manufacturing an ultrafine fiber non-woven fabric by split fiber processing a split fiber type composite fiber web, a melt blow method, a method of producing a non-woven fabric by forming a web using a direct spinning method, a method of forming a non-woven fabric using the island part of a sea-island structured fiber by dissolving the sea part, laser extension or electrospinning can be as a method of forming an ultrafine fiber non-woven fabric. If the label drying pad of the labeling component part related to the present invention is a non-woven fabric including mainly ultrafine fiber having a fiber diameter of 0.05 to 10 µm, then any of the above manufacturing methods can be used but not limited to these methods.

The simple device for a membrane assay of the present invention related to one embodiment is explained below while referring to the diagrams. Furthermore, the embodiments described below are examples of the simple device for a membrane assay of the present invention and the simple device for a membrane assay of the present invention is not limited to these embodiments. In addition, the same reference symbols are attached to the same structural elements therefore a number of explanations are not repeated.

First Embodiment

A lateral flow immunoassay method related to an embodiment of the present invention uses a simple device for a membrane assay which is arranged with membrane linked with a trapping agent for trapping a subject to be detected, and is a simple membrane assay method of a subject to be detected within a sample specimen. The simple device for a membrane assay related to the present embodiment detects or quantifies the presence of a subject to be detected within a sample specimen using a non-woven fabric comprised of ultrafine fibers as a substrate which forms a labeling component part.

In the present specification, a lateral immunoassay method is a method in which a solution which includes the subject to be detected is horizontally developed on a membrane coated with a trapping reagent or agent for detecting which specifically binds to a subject to be detected, forming a composite of a trapping reagent which specifically binds to a subject to be detected, the subject to be detected and a labeling component which specifically binds to a subject to be detected on the membrane, and detecting or quantifying the subject to be detected by detecting or quantifying the labeling component.

Typically, the method reacts a trapping reagent and labeling component with a subject to be detected, a sandwich shaped composite which includes the trapping agent, subject to be detected and labeling component is formed on a membrane and the presence of the composite part is detected by detecting the labeling component. With this method it is possible to simply test for the presence of a subject to be detected within a sample specimen in a short period of time.

FIG. 1 is an exemplary diagram of a simple device for a membrane assay 100 related to the present embodiment. The upper part in FIG. 1 is a planar view and the lower part is a cross sectional view. The simple device for a membrane assay 100 is arranged with a detection part 120, a nitrocellulose membrane 140 formed with a control line 130, an absorption pad 150 formed by filter paper, a label drying pad 160 maintained by drying a labeling component, and a sample supply part 170 arranged for supplying a prepared sample specimen, stacked on a plastic plate 110 which is a support substrate.

One end region of the absorption pad 150 and one end region of the nitrocellulose membrane 140, the other end region of the nitrocellulose membrane 140 and one end region of the label drying pad 160, and the other end region of the label drying pad 160 and one end region of the sample supply part 170 each overlap to form a connected flow path of a lateral flow.

The simple device for a membrane assay 100 related to the present embodiment may have a known structure apart from using a non-woven fabric (ultrafine fiber non-woven fabric) mainly including ultrafine fibers as the label drying pad 160.

(Ultrafine Fiber Non-Woven Fabric for Label Drying Pad)

Ultrafine fiber non-woven fabric used for the label drying pad related to the present embodiment is explained below in detail. A manufacturing method of ultrafine fiber non-woven fabric for the label drying pad related to the present embodiment is explained using a split fiber processing method of a split fiber type composite fiber web as an example.

Here, a composite fiber refers to a plurality of fiber components each linked in the length direction of the fiber and mutually attached to each other on their side surfaces, and includes two or more types of fiber components with different materials. In addition, split fiber type composite fiber refers to a composite fiber which includes a structure in which each fiber component which forms the composite fiber is separable.

Figure 2:
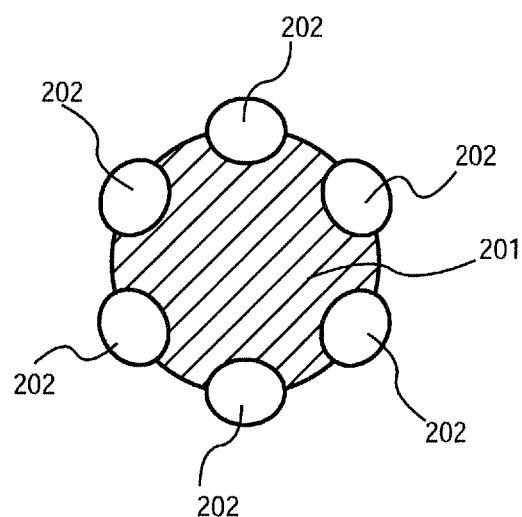
FIG. 2 is an exemplary diagram of a split fiber type composite fiber 200 related to one embodiment of the present invention.

FIG. 2 is an exemplary diagram which shows an example of a structure of a split fiber type composite fiber 200. The split fiber type composite fiber 200, for example, includes a core fiber component 201 and a fiber component of ultrafine split fiber 202.

The split fiber type composite fiber 200, for example, is preferred to have a structure in which a plurality of fiber components of ultrafine split fiber 202 with a fiber diameter from 1 μm to 10 μm are arranged on a cross sectional exterior periphery of the core fiber component 201 with a fiber diameter from 6 μm to 20 μm.

In addition, a structure in which a plurality of ultrafine fiber components 202 are arranged on the cross sectional exterior of the core fiber component 201 is shown as one example of the split fiber type composite fiber 200. However, the structure may also be a two layer type parallel structured split fiber in which two fiber components having a fiber diameter from 1 μm to 10 μm are joined, and a multi layer type parallel multiple structured split fiber type composite fiber in which two fiber components having a fiber diameter from 1 μm to 10 μm are alternately stacked.

Considering strength it is possible to use a synthetic fiber such as nylon, vinylon, acrylic, polyolefin, polyurethane, polyester etc as a material for forming each fiber related to the present embodiment. In the split fiber type composite fiber 200, it is a preferred example that the core fiber component 201 is comprised from a polyolefin resin such as polyethylene resin and the fiber component of ultrafine split fiber is comprised form polyester resin. In the case where a non-woven fabric comprised from these materials is used in the label drying pad 160, the release efficiency of the labeling component from the label drying pad 160 is improved.

The ultrafine fiber non-woven fabric related to the present embodiment is manufactured, for example, by a spunbonding method which is a method for obtaining a long fiber non-woven fabric. Because the fiber length of a fiber produced by a spunbonding method is long, it is possible to provide an ultrafine fiber non-woven fabric which mainly includes this type of fiber having a long fiber length with sufficient tensile strength which is required for an ultrafine fiber non-woven fabric for the label drying pad of the present embodiment. If the ultrafine fiber non-woven fabric for the label drying pad of the present embodiment mainly includes a fiber component of ultrafine fiber comprised of a fiber diameter from 1 μm to 10 μm, it may be manufactured using a melt blown method etc.

When the split fiber type composite fiber 200 is manufactured, the split fiber type composite fiber is split into each fiber component by, for example, a spun lace method of hitting the split fiber type composite fiber with high pressure water, a method of heating, a method which matches an adhesion method between the fiber components such as a method for immersing in a solvent, or a needle punching method.

Figure 3:
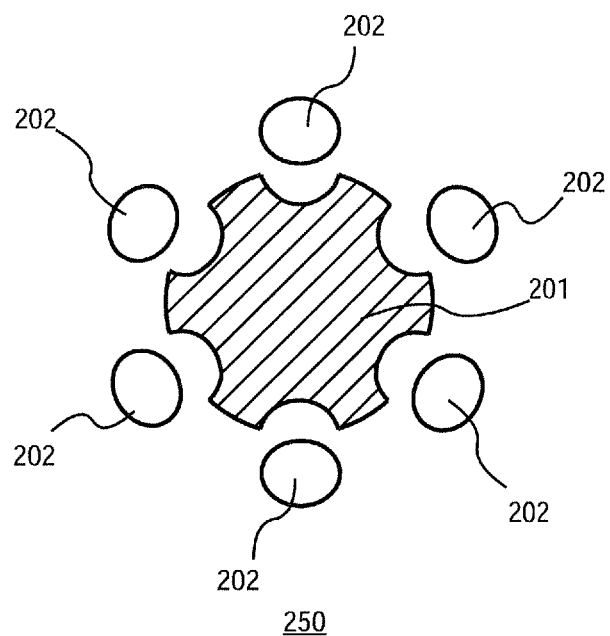
FIG. 3 is an exemplary diagram of a split fiber type composite fiber 250 which has been split processed related to one embodiment of the present invention.

FIG. 3 is an exemplary diagram which shows a composite fiber 250 after split fiber processing. The composite fiber 250 is split into the core split fiber 201 which includes a fiber diameter from 6 μm to 20 μm, and ultrafine fiber 202 which includes a fiber diameter from 1 μm to 10 μm, and each fiber is dissociated from each other. The dissociated core split fiber 201 and ultrafine fiber 202 are precisely interlaced and a non-woven fabric is formed.

The case where an ultrafine fiber non-woven fabric mainly including an ultrafine fiber having a fiber diameter from 1 μm to 10 μm and comprised from a split fiber type composite fiber used as the label drying pad is mentioned in the present embodiment. However, a non-woven fabric manufactured by a method other than a split fiber type composite fiber can also be used as the label drying pad as long as it an ultrafine fiber non-woven fabric mainly including ultrafine fibers having a fiber diameter from 0.05 μm to 10 μm.

(Subject to be Detected)

The subject to be detected related to the present embodiment is not limited in any way and may be each type of pathogen, or clinical marker or a substance which can cause an antigen-antibody reaction with an antibody. As a specific example, a virus antigen such as the Influenza virus, Adenovirus, RS virus, HAV, HB's, HIV, Norovirus and Rotavirus, a bacterial antigen such as MRSA, Group A Streptococci, Group B Streptococci and Legionella, a toxin which is produced from bacteria etc, Mycoplasma, Chlamydia Trachomatis, a hormone such as human chorionic gonadotropin, C reaction protein, myoglobin, cardiac troponin, each type of tumor marker, pesticide or environmental hormone can be exemplified.

In this case of using a pathogenic microbe or a substance such as a protein derived from this pathogenic microbe or an antibody to these as the subject to be detected, a pathogen which can outbreak and requires specifying in an extremely short period of time such as the Influenza virus, RS virus, Adenovirus, Group A Streptococci, Mycoplasma pneumoniae, Rotavirus and Norovirus is very useful.

Furthermore, the subject to be detected may be a single antigen which can induce an immune reaction, or a hapten which cannot induce an immune reaction by itself but can be bound with an antibody by an antigen-antibody reaction.

(Trapping Reagent)

As long as the trapping reagent related to the present embodiment has an antigen-antibody reaction with the subject to be detected which is to be immunoassayed, it can be a polyclonal antibody or a monoclonal antibody.

In the simple device for a membrane assay 100 related to the present embodiment, antigen binding fragments of the antibody may be bound to a labeling component together with an antibody or instead of the antibody. Antigen binding fragments refers to antibody fragments such as Fab or $F(ab')_2$ fragment of an antibody for example, which can have an antigen-antibody reaction with a corresponding antibody. These antigen binding fragments are obtained by processing the antibody by a protease such as papain or pepsin and purifying as in commonly known. In addition, it is also possible to use a genetically-engineered antibody or its antigen binding fragments.

(Labeling Component)

A gold colloid particle, a platinum colloid particle, a colored latex particle, a magnetic particle, a fluorescent particle or an enzyme can be exemplified as the labeling component related to the present embodiment.

An antibody which has an antigen-antibody reaction with the subject to be detected and its antigen biding fragments or either of these are bound to the labeling component related to the present embodiment. In this way, the labeling part can bind with the subject to be detected via the antibody or antigen binding fragment. An antibody or antigen binding fragment with different binding properties to the subject to be detected from the above described trapping reagent is preferred to be used as the antibody or antigen binding fragment bound to the labeling component. Because of the binding properties, that is, the region of the subject to be detected which is bound to by an antibody or antigen binding fragment being different, it is possible to prevent competition between the binding region of the trapping reagent and labeling component and avoid a drop in the efficiency of detecting the subject to be detected.

(Label Drying Pad)

A manufacturing method of the label drying pad related to the present invention is explained. In a process for drying the labeling component, the labeling component is dried while attached to fibers of a component used as the label drying pad. A solution including a certain amount of the labeling component is coated on an ultrafine fiber non-woven fabric for label drying pad related to the present embodiment or allowed to permeate the label drying pad using a spray or immersion method. Following this, the label drying pad is dried by warm air drying or natural drying.

The surface area of a fiber per unit length of the ultrafine fiber non-woven fabric related to the present embodiment which mainly including ultrafine fibers having a fiber diameter from 0.05 μm to 10 μm is larger compared to a fiber having a fiber diameter from 10 μm to 30 μm. In this way, the labeling component is dried uniformly over the entire non-woven fabric in a more dispersed state. In addition, the flow of a sample solution is advanced by a capillarity in the ultrafine fiber non-woven fabric related to the present embodiment which mainly including ultrafine fibers.

As a result, because release when reconstructing the dried labeling component is advanced, the supply amount of a component which participates in a reaction to the assay system is improved and the reaction progresses efficiently in the label drying pad related to the present embodiment, it is possible to assay the subject to be detected rapidly with a high sensitivity using an immunoassay sample lateral flow method.

(Assay Method)

Next, an immunoassay method which uses the simple device for a membrane assay related to the present embodiment is explained. First, a sample specimen in which the sample is suspended/extracted in a sample buffer solution for suspension/extraction is prepared. The sample specimen can be prepared using a known technology depending on the subject to be detected.

The sample specimen is supplied to a sample supply pad 170 which is arranged with an assay device which comprises a label drying pad 160 in which an antibody which has an antigen-antibody reaction with a subject to be detected is labeled with a label is arranged on a nitrocellulose membrane 140 stacked on a plastic plate 110, and detection part 120 in which the antibody which has an antigen-antibody reaction with a subject to be detected is solidified into a line shape as a trapping reagent, and a control line 130 in which a substance which can bind the label, for example, a substance which has the same reaction properties as the subject to be detected or an antibody which is bound to the label is solidified into a position on the downstream of a position at which the trapping agent is bound.

Because a label is developed while moving the sample specimen which includes the subject to be detected in a horizontal direction on a membrane due to capillarity, a composite of the subject to be detected and the label is formed if the subject to be detected exists. Furthermore, when the composite of the subject to be detected and the label reaches the detection part 120, a composite of the trapping reagent, subject to be detected and label is formed on this line. The presence of the composite is detected with the label within this composite, and as a result, the presence of the subject to be detected is determined within the sample specimen. In addition, it is possible to confirm for each sample that the label is released from the label drying pad and that the label flows over the membrane bound with the tapping agent using the control line 130 which is a verification part.

Furthermore, the detection part 120 is a region which has an antigen-antibody reaction with the subject to be detected and which solidifies an antibody or its antigen binding fragment which can simultaneously bind to the subject to be detected with an antibody or its antigen binding fragment on the label into a line shape. Other components which do not participate in the reaction are absorbed by an absorption pad 150.

As explained above, the simple device for a membrane assay related to the present invention of the present embodiment has sufficient tensile strength which is required by the label drying pad by using ultrafine fiber non-woven fabric in a label drying pad, improves release efficiency when reconstructing a label dried by advancing the flow of a sample solution by capillarity and can assay a subject to be detected rapidly with a high sensitivity.

Second Embodiment

Figure 4:
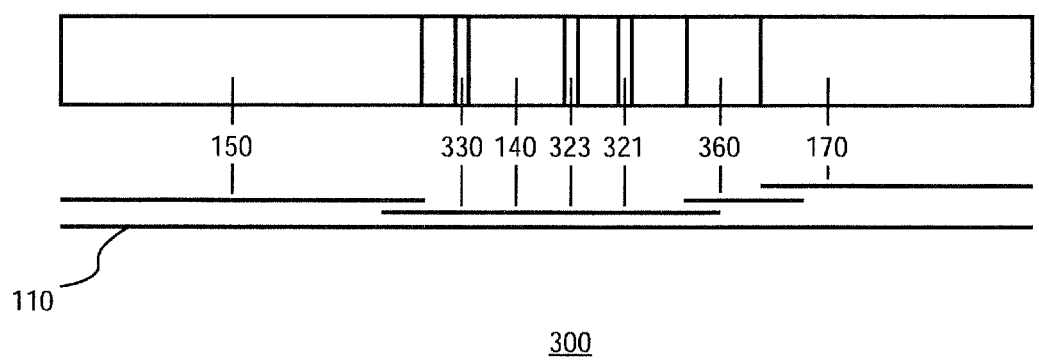
FIG. 4 is an exemplary diagram of a simple device for a membrane assay 300 related to one embodiment of the present invention.

The second embodiment is the same as the first embodiment except that two detection parts are arranged instead of the detection part 120. FIG. 4 is an exemplary diagram which shows a simple device for a membrane assay 300 related to the second embodiment. The simple device for a membrane assay 300 includes a detection part A321 and a detection part B323. In addition, the simple device for a membrane assay 300 also includes a control line 330 and a label drying pad 360 corresponding to a change in the detection part A321 and the detection part B323. While an example in which two detection parts are arranged is described below the number of detection parts is not limited to two.

As described below in the examples, this is for trapping and detecting two types of subject to be detected such as Influenzavirus A and Influenzavirus B respectively. Consequently, an antibody or antigen binding fragment each having a different subject to be detected is solidified into a line shape on the detection part A321 and the detection part 6323.

A plurality of types of subject to be detected can be assayed by arranging a plurality of these detection parts. It is possible to realize a simple device for a membrane assay which detects two or more subjects to be detected in the case where the specificity of antigen-antibody reaction by each antibody or antigen binding fragment is high.

Furthermore, it is possible to detect and identify a plurality of types of subject to be detected by the position of each detection part on a nitrocellulose membrane which is a development part. In addition, in the case where a colored latex particle or fluorescent light emitting particle is used in the label, it is possible to easily identify a subject to be detected by changing the color or fluorescent substance of each label.

In addition, similarly, two types of label which bind an antibody or antigen binding fragment each having a different subject to be detected are created. The created two types of label are allowed to permeate into an ultrafine fiber non-woven fabric which mainly includes a fiber diameter from 0.05 μm to 10 μm explained in the first embodiment and dried on the label drying pad 360.

The label drying pad 360 related to the present embodiment which mainly includes ultrafine fiber is dried more uniformly while the label is dispersed across the entire non-woven fabric than a conventional label drying pad and the flow of a sample solution is more advance due to capillarity.

As a result, release when reconstructing the dried label in the label drying pad related to the present embodiment is advanced, the supply amount of components which participate in the reaction to an assay system is improved and the reaction progresses efficiently. Consequently, by using two or more types of label it is possible to rapidly assay a subject to be detected with a high sensitivity using a lateral flow method immunoassay reagent even in the case where a certain amount per label of one type which is permeated is decreased.

At this time, an antibody or antigen binding fragment which can trap the two types of label described above is solidified into a line shape on the control line 330 related to the present embodiment. In this way, it is possible to confirm for each sample that the labels are released from the label drying part and the labels flow over the membrane bound with the tapping agent.

Constituent features other than these can use components similar components to those in the first embodiment, and by using the simple device for a membrane assay related to the second embodiment it is possible to simultaneously detect a plurality of subjects to be detected using one simple device for a membrane assay.

EXAMPLES

The present invention is explained in more detail below based on examples. However, the present invention is not limited to the examples below.
(Comparison of Physical Properties of a Non-Woven Fabric for Label Drying Pad)

The physical properties used in example 1 and comparative examples 1 to 3 are shown in Table 1.

TABLE 1

| | Materials | Fiber diameter (μm) | | Tensile strength (N/5 cm) | |
| --- | --- | --- | --- | --- | --- |
| | | | | longitudinal | transversal |
| Example 1 | polyester + polyethylene (split fiber processed) | polyester polyethylene | 5 15 | 230 | 95 |
| Comparative example 1 | glass fiber | | 11 | 150 | 80 |
| Comparative example 2 | polyester | | 15 | 250 | 105 |
| Comparative example 3 | polyester + polyethylene (split fiber processed is not performed) | polyester polyethylene | 15 5 | 245 | 100 |

The glass fiber in comparative example 1 has a weak tensile strength and was not suitable for use in a manufacturing machine. Because example 1, comparative example 2 and comparative example 3 are non-woven fabrics comprised of a synthetic fiber, they have strong tensile strength and can be used in a manufacturing machine.
(Assay of Release Rate of a Label from a Label Drying Pad)

The release characteristics of a label drying pad which labels a latex particle in example 1, comparative example 2 and comparative example 3 were evaluated as follows.
(1. Creation of Label Drying Pad for Labeling a Latex Particle)

An anti A type influenza virus antibody and anti B type influenza virus antibody were used as antibodies used for detection. The latex which was used as a label and a latex suspended solution to which the anti influenza virus antibody was covalent bound to was prepared. Each type of fiber composite described above was coated with the prepared latex suspended solution, dried and a label drying pad was created.
(2. Assay of Release Rate of a Latex Particle)

The label drying pad created by the method described above was immersed into a predetermined buffer solution and a latex particle was eluted by stirring. The absorbance of the eluted solution (A) was assayed and the absorbance of a sample (B) was assayed using a solution in which the same amount of a label as the amount coated on the pad was added to the buffer solution as a comparison solution. The release rate of a label from a pad was obtained from the results using the equation shown below.

Release rate (%)=absorbance $A$/absorbance $B$×100

(3. Results)

The obtained results are shown in Table 2.

TABLE 2

|  | release ratio |
| --- | --- |
| Example 1 | ○ |
| Comparative example 1 | Δ |
| Comparative example 2 | Δ |
| Comparative example 3 | X |

○ (good): 100 to 90% of release ratio
Δ (medium): 90 to 80% of release ratio
X (bad): 0 to 70 of release ratio Example 1 has the highest release ratio, comparative example 1 and 2 having the same release ratio with comparative example 3 having the lowest release ratio. It was confirmed that the release ration of a label from example 1 is the highest.

(Detection of Influenza Virus Antigen Using Lateral Flow Immunoassay Method)

(1. Creation of a Test Device)

The simple device for a membrane assay was used with the same structure as that shown in FIG. 4. An anti A type influenza virus antibody and anti type influenza virus antibody were coated in a line shape on a reed shaped component in which the nitrocellulose membrane 140 is backed by the plastic plate 110 and dried well under warm air. An absorption pad 150 is arranged overlapping an upper end of this nitrocellulose membrane 140. Furthermore, a label drying pad 360 is arranged overlapping the lower end of the nitrocellulose membrane 140, and a sample supply pad 170 which supplies a sample is arranged overlapping this label drying pad 360. A piece which covers other parts is cut away at a certain width so that one part of a sample sheet is exposed by the plastic sheet and the test device is created.

(2. Experiment)

An A type influenza virus and type influenza virus were used as a sample. The sample was performed using double serial dilution as a sample specimen using a certain buffer solution for a sample suspension, extraction. Next, the test device was placed in a horizontal position, 50 µL of a sample specimen and a negative contrast specimen comprised from only the certain buffer solution for extraction were supplied to the sample supply pads 170 respectively and a label was developed. Whether a colored line in the detection part existed or not was visually observed after 8 minutes.

Existence of a colored line: positive (+)
Non-existence of a colored line: negative (−)

The same non-woven fabrics used in the experiment described above were also used in example 1 and comparative examples 1 to 3, and the experiment was performed using the non-woven fabrics as the label drying pad 360.

(3. Results)

The detection results of the influenza virus are shown in Table 3. In example 1, the determination of the A type influenza virus showed positive up to 1:3200, the detection sensitivity being high compared to determination from comparative example 1 to comparative example 3 with respect to the type A. In addition, in example 1, the determination of the B type influenza virus showed positive up to 1:1600, sensitivity being high compared to determination from comparative example 1 to comparative example 3 with respect to the type B. Furthermore, the negative contrast specimen showed negative in all the examples and comparative example.

In example 1, a less amount of the A type influenza virus is detected than in comparative example 1 to 3. A less amount of the B type influenza virus is also detected in example 1 than in comparative example 1 to 3. The result of this detection sensitivity experiment reflects the assay results of the release ratio of the label described above, wherein the level of detection sensitivity increases when the release ratio of a label increases.

It was found that by using the label drying pad related to the embodiments of the present invention, it is possible to improve the release ratio of a label from the label drying pad and detect an A type and B type influenza virus with a high sensitivity.

TABLE 3

| Test sample | | Example 1 | Comparative example 1 | Comparative example 2 | Comparative example 3 |
| --- | --- | --- | --- | --- | --- |
| Type A | 1:800 | + | + | + | + |
|  | 1:1600 | + | + | + | − |
|  | 1:3200 | + | − | − | − |
|  | 1:6400 | − | − | − | − |
| Type B | 1:400 | + | + | + | + |
|  | 1:800 | + | + | + | − |
|  | 1:1600 | + | − | − | − |
|  | 1:3200 | − | − | − | − |

According to the present invention, a simple device for membrane assay is provided using the lateral flow immunoassay method, whereby a subject to be detected can be detected at a high sensitivity, provided with as label drying pad, a substrate which has a higher tensile strength than glass fiber and can well release a label.

The invention claimed is:

1. A device for a membrane assay using a lateral flow immunoassay method comprising:
    a sample supply part which supplies a sample containing a subject to be detected;
    a labeling component part containing a labeling component which labels a subject to be detected in the sample from the sample supply part;
    a development part formed with a detection part which includes a trapping reagent for detecting or quantifying the labeled subject to be detected from the sample; and
    an absorption part which receives the sample from the detection part;
    wherein
    a non-woven fabric comprises fibers as the labeling component part,
    the labeling component part of said non-woven fabric consists of a split fiber type composite fiber having a structure arranged with a plurality of second fiber components consisting of polyester resin with a fiber diameter from 0.05 µm to 10 µm on a cross sectional exterior periphery of a first fiber component consisting of a polyolefin resin with a fiber diameter from 6 µm to 20 µm, and
    the first fiber component and the plurality of second fiber components are interlaced.

2. The device for a membrane assay according to claim 1, wherein the labeling component is labeled by any one of a gold colloid particle, a platinum colloid particle, a latex particle, a magnetic particle and an enzyme.

3. The device for a membrane assay according to claim 2, wherein the labeling component and the trapping reagent are either one of antibody and antigen binding fragments which bind with the subject to be detected.

4. The device for a membrane assay according to claim 3, wherein the subject to be detected is at least one of a microbe, a biological derived material which is a clinical marker, a pesticide, an environmental hormone and a decomposed matter of these.

5. The device for a membrane assay according to claim 4, wherein the subject to be detected is detected or quantified using a lateral flow membrane assay method.

6. The device for a membrane assay according to claim 5, further comprising: a verification part for verifying that the labeling component is released to the development part.

7. The device for a membrane assay according to claim 6, wherein a plurality of types of labeling component and trapping reagent are used respectively for detecting a plurality of types of the subject to be detected.

8. The device for a membrane assay according to claim 2, wherein a release rate of the labeling component part from the non-woven fabric is more than 70%, wherein the labeling component is a latex particle.

9. The device for a membrane assay according to claim 1, wherein the second fiber components comprise a polyester and the first fiber component comprising a polyethylene.

10. The device for membrane assay according to claim 1, wherein the non-woven fabric consists of a split fiber type composite fiber having a tension strength higher than 80 N/5 cm to a longitudinal direction and a transversal direction.

* * * * *